United States Patent [19]

Wise et al.

[11] Patent Number: 5,780,717
[45] Date of Patent: Jul. 14, 1998

[54] IN-LINE REAL TIME AIR MONITOR

[75] Inventors: Marcus B. Wise, Kingston; Cyril V. Thompson, Knoxville, both of Tenn.

[73] Assignee: Lockheed Martin Energy Research Corporation, Oak Ridge, Tenn.

[21] Appl. No.: 838,954

[22] Filed: Apr. 23, 1997

[51] Int. Cl.[6] .................... G01N 30/14; G01N 9/32; G01N 27/16; H01J 49/04
[52] U.S. Cl. .............. 73/23.2; 73/23.41; 73/23.35; 73/864.81; 73/23.42; 422/83; 422/93
[58] Field of Search .................. 73/23.2, 31.02, 73/31.03, 863.61, 864.81, 23.37, 23.35, 23.41, 23.42; 422/82, 83, 93

[56] References Cited

U.S. PATENT DOCUMENTS

| | | | |
|---|---|---|---|
| 3,991,626 | 11/1976 | Shair | 73/421.5 R |
| 4,101,282 | 7/1978 | Ririe | 23/254 R |
| 4,259,573 | 3/1981 | Prober et al. | 250/287 |
| 4,341,108 | 7/1982 | Warncke et al. | 73/23 |
| 4,348,887 | 9/1982 | Lorenz et al. | 73/23 |
| 4,635,735 | 1/1987 | Crownover | 175/48 |
| 4,709,575 | 12/1987 | Myers | 73/23 |
| 4,826,775 | 5/1989 | Burns et al. | 436/179 |
| 5,012,052 | 4/1991 | Hayes | 250/288 |
| 5,041,265 | 8/1991 | Koike et al. | 422/94 |
| 5,161,406 | 11/1992 | Heinonen | 73/23.2 |
| 5,245,857 | 9/1993 | Kahl | 73/23.2 |
| 5,272,337 | 12/1993 | Thompson et al. | 250/288 |
| 5,325,705 | 7/1994 | Tom | 73/31.03 |
| 5,395,589 | 3/1995 | Nacson | 422/88 |
| 5,401,468 | 3/1995 | Patashnick et al. | 422/80 |
| 5,435,169 | 7/1995 | Mitra | 73/23.41 |
| 5,531,096 | 7/1996 | Castor | 73/23.2 |
| 5,542,284 | 8/1996 | Layzell et al. | 73/23.2 |
| 5,547,497 | 8/1996 | Klemp et al. | 96/104 |

OTHER PUBLICATIONS

Marcus B. Wise, Cyril V. Thompson, Michelle V. Buchanan, Roosevelt Merriweather and Michael R. Guerin "Direct Sampling Ion Trap Mass Spectrometry," Spectroscopy 8(5) Jun. 1993, pp. 14–22.

Primary Examiner—Hezron E. Williams
Assistant Examiner—J. David Wiggins
Attorney, Agent, or Firm—Ivan L. Ericson

[57] ABSTRACT

An in-line gas monitor capable of accurate gas composition analysis in a continuous real time manner even under strong applied vacuum conditions operates by mixing an air sample with helium forming a sample gas in two complementary sample loops embedded in a manifold which includes two pairs of 3-way solenoid valves. The sample gas is then analyzed in an ion trap mass spectrometer on a continuous basis. Two valve drivers actuate the two pairs of 3-way valves in a reciprocating fashion, so that there is always flow through the in-line gas monitor via one or the other of the sample loops. The duty cycle for the two pairs of 3-way valves is varied by tuning the two valve drivers to a duty cycle typically between 0.2 to 0.7 seconds.

20 Claims, 3 Drawing Sheets

5,780,717

IN-LINE REAL TIME AIR MONITOR

Statement as to Rights to Inventions made under Federally-Sponsored Research and Development This invention was made with Government support under contract DE-AC05-96OR22464 awarded by the U.S. Department of Energy to Lockheed Martin Energy Research Corporation and the Government has certain rights in this Invention.

FIELD OF THE INVENTION

The present invention relates to a gas monitor, more particularly, to a continuous gas monitor for a gas analyzer.

BACKGROUND OF THE INVENTION

Previous real time gas monitors, such as the one previously developed and patented, U.S. Pat. No. 5,272,337, by the inventors of the present invention, have been subject to operational degradation from pressure fluctuation, chemical memory effects, and difficulty in tuning, with the memory effects being the most difficult problem to overcome. Such gas monitors cannot operate where a strong vacuum is required, due to the perturbations of the vacuum on the mixing of the gas sample with helium buffer gas, the mix being required for successful analysis of the gas sample by a mass spectrometer. Although such gas monitors can be used to sample the effluent from a much stronger vacuum pump in situations where such a vacuum is required (sampling through long, small diameter transfer lines), the heads of even the most invert vacuum pumps tend to retain significant amounts of the chemicals sampled through adsorption of the chemicals into the head and diaphragm materials. The present in-line real time gas monitor overcomes this problem through a unique design which permits in-line sampling, even in situations where a significant vacuum is necessitated.

OBJECTS OF THE INVENTION

Accordingly, it is an object of the present invention to provide a gas monitor for analyzing gas samples continuously in real time. Further and other objects of the present invention will become apparent from the description contained herein.

SUMMARY OF THE INVENTION

In accordance with one aspect of the present invention, a new and improved continuous in-line gas monitoring system comprises: an in-line monitor, a source of sample gas, a supply of carrier gas having a carrier gas outlet port, a gas analyzer having a gas inlet port and a vacuum source having a gas inlet port.

The in-line monitor comprises: a sample gas passage having a gas inlet port and a gas outlet port, a carrier gas passage having a gas inlet port and a gas outlet port, a gas analyzer passage having a gas outlet port and a gas inlet port, a vacuum passage having a gas outlet port and a gas inlet port, a first gas mixing passage having a gas inlet port and a gas outlet port, a second gas mixing passage having a gas inlet port and a gas outlet port and a sample gas transfer means for simultaneously positioning the first gas mixing passage and the second gas mixing passage from a first position to a second position. The first position causes positioning and connecting of the first gas mixing passage with the sample gas passage and the vacuum passage and the second gas mixing passage with the carrier gas passage and the gas analyzer passage. The second position causes positioning and connecting of the first gas mixing passage with the carrier gas passage and the gas analyzer passage and the second gas mixing passage with the sample gas passage and the vacuum passage. The positioning and connecting of the sample gas passage, the first gas mixing passage and the vacuum passage provides for the sample gas to be transferred into and through the sample gas passage, the first gas mixing passage and the vacuum passage by the vacuum source filling the first gas mixing passage with the sample gas at a reduced pressure. The positioning and connecting of the carrier gas passage, the second gas mixing passage and the gas analyzer passage provides for the carrier gas from the carrier gas source to be transferred into and through the carrier gas passage, second gas mixing passage and the gas analyzer passage filling the second gas mixing passage with the carrier gas at a pressure greater than the reduced pressure of the sample gas contained in the first gas mixing passage. The simultaneous positioning of the first gas mixing passage and the second gas mixing passage from a first position to a second position causes the sample gas contained in the first gas mixing passage to mix with the carrier gas flowing through the carrier gas passage into the first gas mixing passage containing the sample gas and through the gas analyzer passage into the gas analyzer and causes the carrier gas contained in the second gas mixing passage to mix with the sample gas flowing through the sample gas passage into the second gas mixing passage containing the carrier gas and through the vacuum passage into the vacuum source. A reciprocating of the simultaneous positioning of the first gas mixing passage and the second gas mixing passage through a sufficient duty cycle rate causes a mixing of the sample gas with the carrier gas forming a sample gas mixture because of a difference in the gas pressure of the sample gas and the gas pressure of the carrier gas.

At the first position the sample gas is in communication with the inlet port of the sample gas passage, the gas outlet port of the sample gas passage is connected to the gas inlet port of the first gas mixing passage, the gas outlet port of the first gas mixing passage is connected to the gas inlet port of the vacuum passage and the gas outlet port of the vacuum passage is connected to the gas inlet port of the vacuum source and the gas inlet port of the carrier gas passage is connected to the gas outlet port of the supply of carrier gas, the gas inlet port of the second gas mixing passage is connected to the gas outlet port of the carrier gas passage, the outlet port of the second gas mixing passage is connected to the gas inlet port of the gas analyzer passage, the gas outlet port of the gas analyzer passage is connected to the gas inlet port of the gas analyzer.

At the second position the sample gas is in communication with the inlet port of the sample gas passage, the gas outlet port of the sample gas passage is connected to the gas inlet port of the second gas mixing passage, the gas outlet port of the second gas mixing passage is connected to the gas inlet port of the vacuum passage and the gas outlet port of the vacuum passage is connected to the gas inlet port of the vacuum source and the gas inlet port of the carrier gas passage is connected to the gas outlet port of the supply of carrier gas, the gas inlet port of the first gas mixing passage is connected to the gas outlet port of the carrier gas passage, the outlet port of the first gas mixing passage is connected to the gas inlet port of the gas analyzer passage, the gas outlet port of the gas analyzer passage is connected to the gas inlet port of the gas analyzer.

In accordance with another aspect of the present invention, a new and improved method for continuously monitoring a gas sample with a gas analyzer comprises the following steps:

Step 1—A continuous in-line gas monitoring system is provided. The continuous in-line gas monitoring system comprises: an in-line monitor, a source of sample gas, a supply of carrier gas having a carrier gas outlet port, a gas analyzer having a gas inlet port and a vacuum source having a gas inlet port.

The in-line monitor comprises: a sample gas passage having a gas inlet port and a gas outlet port, a carrier gas passage having a gas inlet port and a gas outlet port, a gas analyzer passage having a gas outlet port and a gas inlet port, a vacuum passage having a gas outlet port and a gas inlet port, a first gas mixing passage having a gas inlet port and a gas outlet port, a second gas mixing passage having a gas inlet port and a gas outlet port and a sample gas transfer means for simultaneous positioning the first gas mixing passage and the second gas mixing passage from a first position to a second position. The first position causes positioning and connecting of the first gas mixing passage with the sample gas passage and the vacuum passage and the second gas mixing passage with the carrier gas passage and the gas analyzer passage. The second position causes positioning and connecting of the first gas mixing passage with the carrier gas passage and the gas analyzer passage and the second gas mixing passage with the sample gas passage and the vacuum passage. The positioning and connecting of the first gas mixing passage with the sample gas passage and the vacuum passage provides for the sample gas to be transferred into and through the sample gas passage, the first gas mixing passage and the vacuum passage by the vacuum source filling the first gas mixing passage with the sample gas at a reduced pressure. The positioning and connecting of the first gas mixing passage with the carrier gas passage and the gas analyzer passage provides for the carrier gas from the carrier gas source to be transferred into and through the carrier gas passage, the second gas mixing passage and the gas analyzer passage filling the second gas mixing passage with the carrier gas at a pressure greater than the reduced pressure of the sample gas contained in the first gas mixing passage. The simultaneous positioning of the first gas mixing passage and the second gas mixing passage from a first position to a second position causes the sample gas contained in the first gas mixing passage to mix with the carrier gas flowing through the carrier gas passage into the first gas mixing passage containing the sample gas and through the gas analyzer passage into the gas analyzer and causes the carrier gas contained in the second gas mixing passage to mix with the sample gas flowing through the sample gas passage into the second gas mixing passage containing the carrier gas and through the vacuum passage into the vacuum source. A reciprocating of the simultaneous positioning of the first gas mixing passage and the second gas mixing passage through a sufficient duty cycle rate causes a mixing of the sample gas with the carrier gas because of a difference in the gas pressure of the sample gas and the gas pressure of the carrier gas. At the first position, the sample gas is in communication with the inlet port of the sample gas passage. The gas outlet port of the sample gas passage is connected to the gas inlet port of the first gas mixing passage. The gas outlet port of the first gas mixing passage is connected to the gas inlet port of the vacuum passage and the gas outlet port of the vacuum passage is connected to the gas inlet port of the vacuum source. The gas inlet port of the carrier gas passage is connected to the gas outlet port of the supply of carrier gas. The gas inlet port of the second gas mixing passage is connected to the gas outlet port of the carrier gas passage. The outlet port of the second gas mixing passage is connected to the gas inlet port of the gas analyzer passage. The gas outlet port of the gas analyzer passage is connected to the gas inlet port of the gas analyzer. At the second position the sample gas is in communication with the inlet port of the sample gas passage. The gas outlet port of the sample gas passage is connected to the gas inlet port of the second gas mixing passage. The gas outlet port of the second gas mixing passage is connected to the gas inlet port of the vacuum passage. The gas outlet port of the vacuum passage is connected to the gas inlet port of the vacuum source. The gas inlet port of the carrier gas passage is connected to the gas outlet port of the supply of carrier gas. The gas inlet port of the first gas mixing passage is connected to the gas outlet port of the carrier gas passage. The outlet port of the first gas mixing passage is connected to the gas inlet port of the gas analyzer passage. The gas outlet port of the gas analyzer passage is connected to the gas inlet port of the gas analyzer.

Step 2—The inlet port of the sample gas passage is positioned at a gas sample source.

Step 3—A flow of the carrier gas is provided into the carrier gas passage.

Step 4—The vacuum source is provided at the gas outlet port of the vacuum passage.

Step 5—The gas analyzer is provided at the gas outlet port of the gas analyzer passage.

Step 6—The sample gas transfer means is activated to simultaneously position the first gas mixing passage and the second gas mixing passage from the first position to the second position in a reciprocating fashion to provide a continuous flow of the gas sample, a continuous mixing of the carrier gas with the gas sample forming a sample gas mixture and a continuous flow of the sample mixture to the gas analyzer.

Step 7—The gas sample containing the sample gas mixture is analyzed with the gas analyzer.

For a better understanding of the present invention, together with other and further objects, advantages and capabilities thereof, reference is made to the following disclosure and appended claims in connection with the above described drawings.

DETAILED DESCRIPTION OF THE PREFERRED EMBODIMENTS

Figure 1:
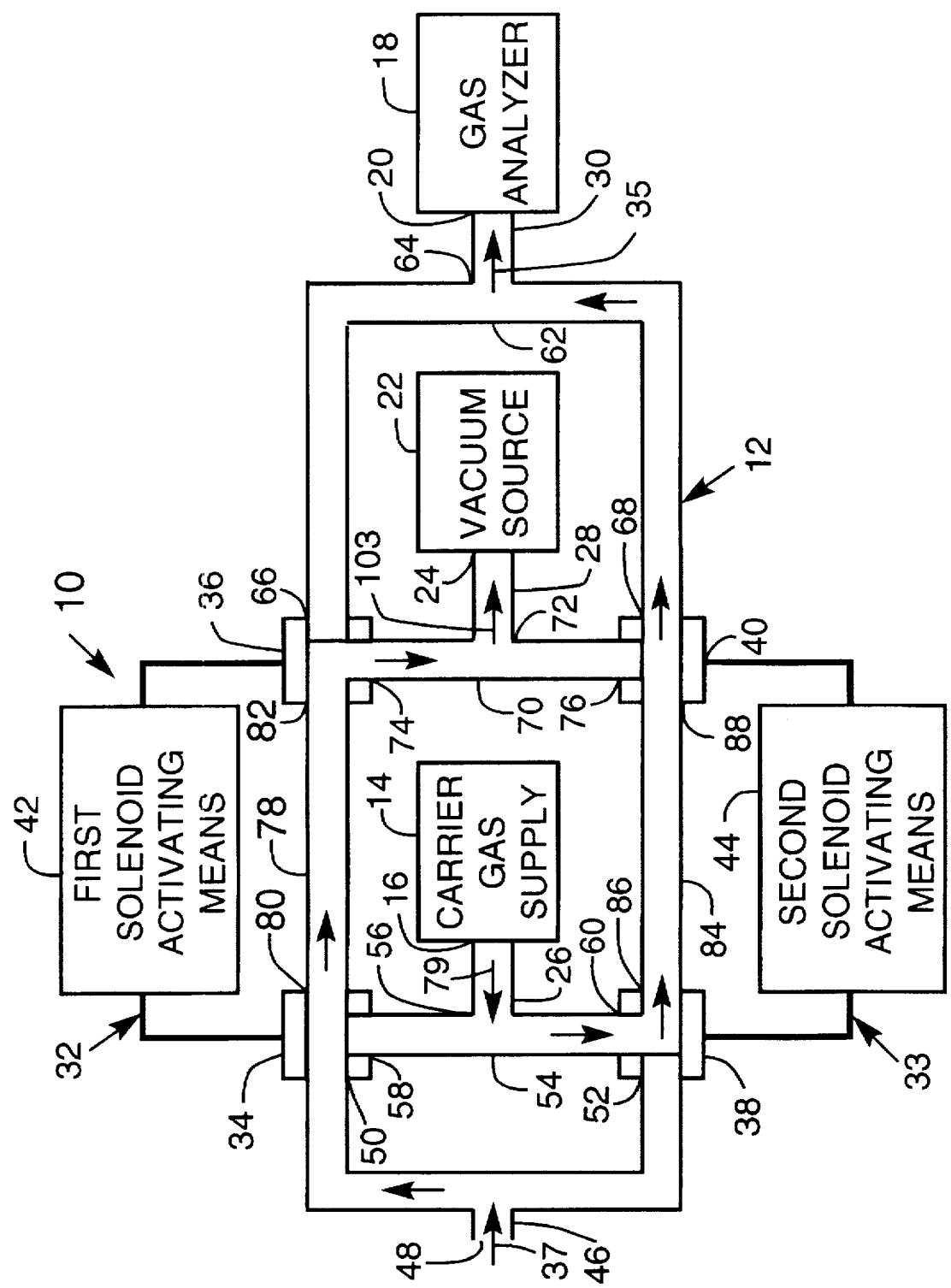
FIG. 1. is a cross-sectional view of an in-line gas monitoring system showing the first position of the gas passages of the in-line monitor in accordance with the present invention.
Figure 2:
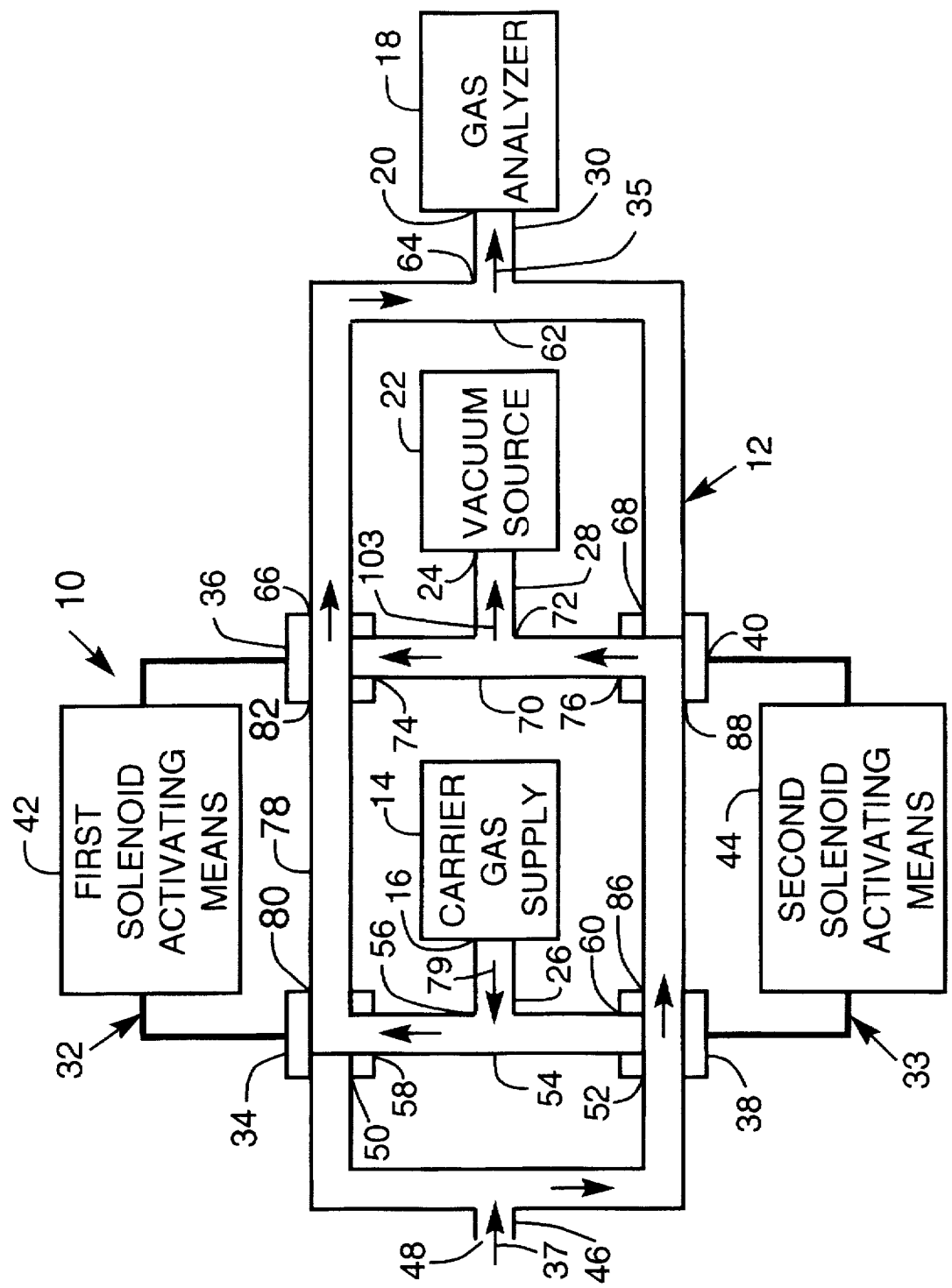
FIG. 2. is a cross-sectional view of an in-line gas monitoring system showing the second position of the gas passages of the in-line monitor in accordance with the present invention.
Figure 3:
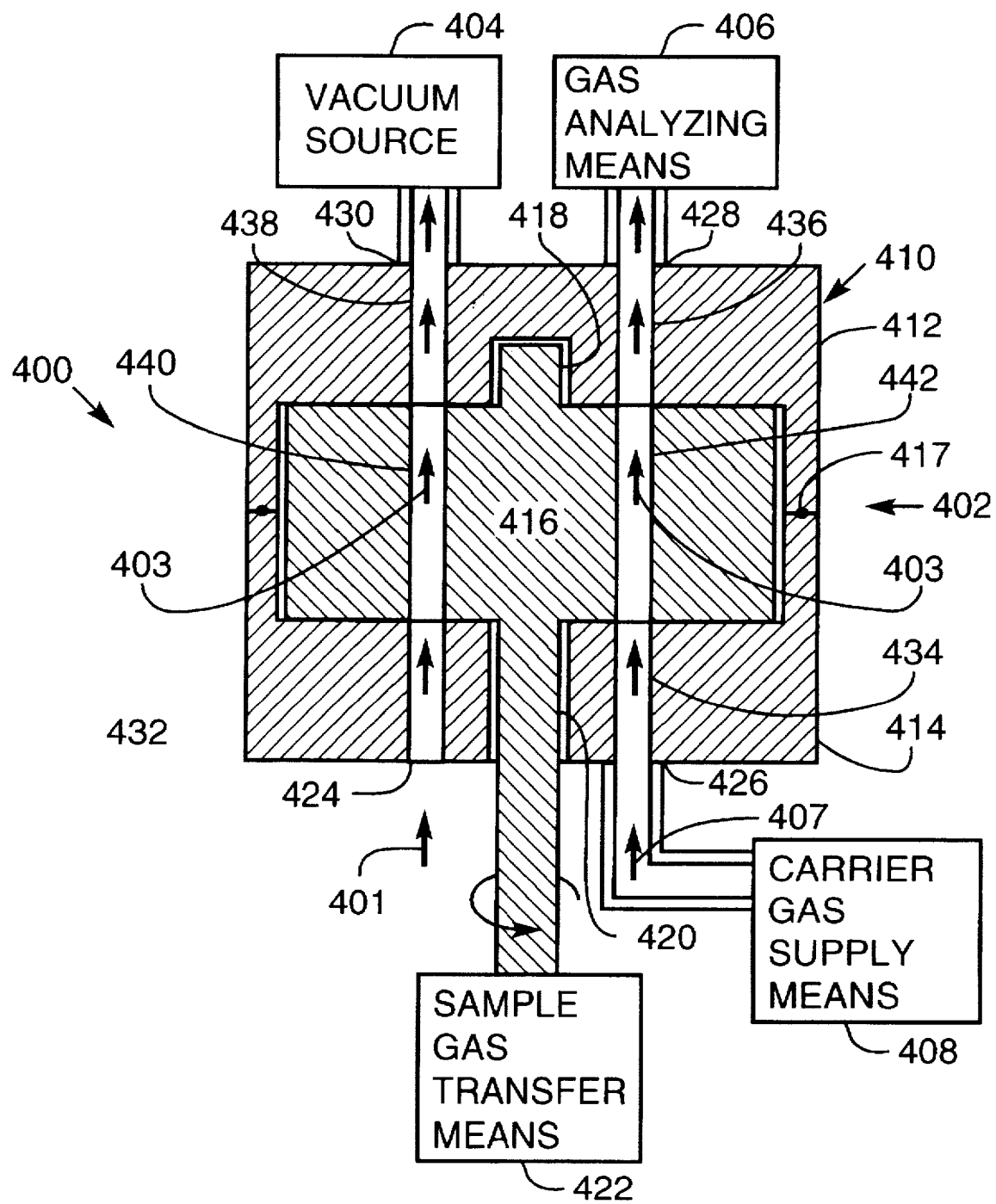
FIG. 3. is a cross-sectional view of another embodiment of an in-line gas monitoring system in accordance with the present invention.

The in-line gas monitoring system comprises an in-line gas monitor coupled together with a mass spectrometer, a carrier gas source and a vacuum source to enable an operator to monitor an atmosphere continuously. The in-line gas monitor operates by mixing a gas sample, such as air, with a carrier gas, such as helium, in two complementary gas passages embedded in a manifold which includes four 3-way solenoid valves having valve activating means or a rotating member having two complementary gas passages which rotates within a manifold. A vacuum source connected to the in-line monitor provides a negative pressure within the in-line monitor which causes an outside source of gas to be continuously drawn into the in-line monitor and out through the vacuum source as a flush gas. At the same time a continuous flow of carrier gas, such as helium, is provided within the in-line monitor which mixes with the gas sample every time the two complementary gas passages are exchanged by the activation of the two sets of solenoid valves or the rotation of the rotating member within the manifold. The differential pressure between the gas sample within the in-line monitor and the carrier gas causes the two gases to mix thoroughly. There are two path ways for the incoming gas sample and the carrier gas to be mixed and carried into a gas analyzer. The first position of the gas mixing passages is shown in FIG. 1 and and the second position of the gas mixing passages is shown in FIG. 2. The gas sample mixes with the carrier gas when two solenoid valve activating means activate the two sets of solenoid valves or when the rotating member rotates 180 degrees as shown in FIG. 3.

The operation of the in-line air monitor of the present invention is based on the generation of a pressure differential between the air sample drawn into the manifold by the vacuum pump and the subsequent helium carrier gas injection, which moves the air sample into an ion trap mass spectrometer. The ion trap mass spectrometers operate by sweeping the ions from the analyzer on a time scale of milliseconds. In the optimized operation of the air monitor, the vacuum pump draws an air sample into a gas passage through a needle valve. The needle valve is partially closed, creating a partial vacuum in the gas passage. When the gas passages are reciprocated, the helium carrier gas is introduced under pressure into the gas passage containing the air sample at a partial vacuum. The helium carrier gas and air sample are turbulently mixed, with the mixture being introduced into the mass spectrometer for analysis. The mixture is necessary to ensure proper analysis, as too much helium dilutes the sample and too much air sample causes signal degradation.

If the air monitor is operated without the proper partial vacuum (pressure differential between the helium carrier gas and the air sample) in the gas passages, the introduction of the helium carrier gas into the gas mixing passage after the air sample is resident in the gas mixing passage, will result in the air sample and the helium carrier gas being introduced into the ion trap mass spectrometer as separate slugs of gas rather than as an essentially homogeneous mixture of the helium carrier gas and the air sample. Separate slugs of the helium carrier gas and the air sample entering the ion trap mass spectrometer causes signal degradation because the ion trap mass spectrometer sees either sample or helium carrier gas, rather than the essentially homogeneous mixture of the helium carrier gas and the air sample required for an appropriate analysis of the air sample.

The in-line gas monitor is unique in its ability to function in-line with a transfer line under a vacuum. It is also more sensitive and much more easily tuned than the gas monitor discussed in U.S. Pat. No. 5,272,337. The in-line gas monitor of the present invention can be constructed as a high temperature gas monitor for use as a stack gas monitor on incinerators, furnaces or other high temperature exhaust gas streams.

In addition, the in-line gas monitor of the present invention can be used to monitor industrial/chemical processes, the levels of chemicals in work-place air, stack gases, soil gases, as a locator of point pollution sources, to track plumes of chemicals in air, etc.

Shown in FIGS. 1 and 2 is continuous in-line gas monitoring system 10 comprising in-line monitor 12; sample gas transfer means 32 and 33 of in-line monitor 12; carrier gas supply 14, such as a cylinder of helium connected to a regulator and a flow control valve, having carrier gas output port 16 and gas passage 26; gas analyzer 18, such as a ion trap mass spectrometer as described in U.S. Pat. No. 5,272,337 to Thompson et al incorporated herein by reference thereto, having a gas inlet port 20 and gas passage 30; and vacuum source 22, such as a vacuum pump, having inlet port 24 and gas passage 28. Carrier gas supply 14 is connected to in-line gas monitor 12 by carrier gas passage 26. Vacuum source 22 is connected to in-line monitor 12 by gas passage 28. Gas analyzer 18 is connected to in-line monitor 12 by gas passage 30.

Shown in FIG. 1 is in-line gas monitor 12 in a first position and shown in FIG. 2 is in-line gas monitor 12 in a second position. Shown in FIG. 1 and FIG. 2 is sample gas transfer means 32 and 33 of in-line monitor 12. Sample gas transfer means 32 comprises first 3-way solenoid valve 34, second 3-way solenoid valve 36 and first solenoid valve activating means 42 such as a solenoid valve driver which actuates the pair of solenoid valves 34 and 36. Sample gas transfer means 33 comprises third 3-way solenoid valve 38, fourth 3-way solenoid valve 40 and second solenoid valve activating means 44, such as a solenoid valve driver which actuates the pair of solenoid valves 38 and 40. The activation of first solenoid valve activating means 42 and of second solenoid valve activating means 44 occurs in a reciprocating fashion, so that there is always flow through in-line gas monitor 12 via the gas passages of the first position of in-line gas monitor 12 shown in FIG. 1 or through the second position of in-line gas monitor 12 shown in FIG. 2. The duty cycle for solenoid valve pairs 34, 36 and 38, 40 is varied by tuning with a potentiometer and is typically 0.2 to 0.7 seconds.

Shown in FIG. 1 and 2 is in-line monitor 12 comprising: sample gas passage 46 8 having sample gas inlet port 48, first sample gas outlet port 50 and second sample gas outlet port 52, carrier gas passage 54 having gas inlet port 56, first gas outlet port 58 and second gas outlet port 60, gas analyzer passage 62 having gas outlet port 64, first gas inlet port 66 and second gas inlet port 68, vacuum gas passage 70 having a gas outlet port 72, first gas inlet port 74 and second gas inlet port 76, first gas mixing passage 78 having gas inlet port 80 and gas outlet port 82, second gas mixing passage 84 having gas inlet port 86 and gas outlet port 88, sample gas transfer means 32 for transferring sample gas and sample gas transfer means 33 for transferring sample gas. First sample transfer means 32 comprises first 3-way solenoid valve 34, second 3-way solenoid valve 36 and first solenoid valve activating means 42. Second sample gas transfer means 33 comprises third 3-way solenoid valve 38, fourth 3-way solenoid valve 40 and second solenoid valve activating means 44.

First 3-way solenoid valve 34 is connected to first sample gas outlet port 50 of sample gas passage 46, first sample gas outlet 58 of carrier gas passage 54 and gas inlet port 80 of first gas mixing passage 78. Second 3-way solenoid valve 36 is connected to first gas inlet port 66 of gas analyzer passage 62, first gas inlet port 74 of vacuum gas passage 70 and gas outlet port 82 of first gas mixing passage 78. Third 3-way solenoid valve 38 is connected to second sample gas outlet port 52 of sample gas passage 46, second gas outlet port 60 of carrier gas passage 54 and gas inlet port 86 of second gas mixing passage 84. Fourth 3-way solenoid valve 40 is connected to second gas outlet port 76 of vacuum gas passage 70, second gas inlet port 68 of gas analyzer passage 62 and gas outlet port 88 of second gas mixing passage 84.

Sample gas transfer means 32 and 33 transfer sample gas by simultaneous positioning first gas mixing passage 78 and second gas mixing passage 84 from a first position to a second position. The first position causes positioning and connecting of first gas mixing passage 78 with sample gas passage 46 and vacuum passage 70 which is connected to gas passage 28 of vacuum source 22 at vacuum source inlet 24 and causes positioning and connecting of second gas mixing passage 84 with carrier gas passage 54 and gas analyzer passage 62. Gas analyzer passage 62 is connected to gas passage 30 of gas analyzer 18 at gas inlet port 20 of gas analyzer 18. The second position causes positioning and connecting of first gas mixing passage 78 with carrier gas passage 54 and gas analyzer passage 62 and causes positioning and connecting of second gas mixing passage 84 with sample gas passage 46 and vacuum passage 70. The positioning and connecting of sample gas passage 46, first gas mixing passage 78 and vacuum passage 62 provides for sample gas 37 to be transferred into and through sample gas passage 46, first gas mixing passage 78 and vacuum passage 70 by vacuum source 22 filling first gas mixing passage 78 with sample gas 37 at a reduced pressure (see FIG. 1). The positioning and connecting of carrier gas passage 54, second gas mixing passage 84 and gas analyzer passage 62 provides for carrier gas 79 from carrier gas source 14 to be transferred into and through carrier gas passage 54, second gas mixing passage 84 and gas analyzer passage 62 filling second gas mixing passage 84 with carrier gas 79 at a pressure greater than the reduced pressure of sample gas 37 contained in first gas mixing passage 78. The simultaneous positioning of first gas mixing passage 78 and second gas mixing passage 84 from a first position to a second position causes sample gas 37 contained in first gas mixing passage 78 to mix with carrier gas 79 flowing through carrier gas passage 54 into first gas mixing passage 78 containing sample gas 37 and through gas analyzer passage 62 into gas analyzer 18 and causes carrier gas 79 contained in second gas mixing passage 84 to mix with sample gas 37 flowing through sample gas passage 46 into second gas mixing passage 84 containing carrier gas 79 and through vacuum passage 70 into vacuum source 22. A reciprocating of the simultaneous positioning of first gas mixing passage 78 and second gas mixing passage 84 through a sufficient duty cycle rate causes a mixing of sample gas 37 with carrier gas 79 forming sample gas mixture 35 comprising a mixture of sample gas 37 and carrier gas 79 because of a difference in the gas pressure of sample gas 37 and the gas pressure of carrier gas 79.

At the first position, shown in FIG. 1, sample gas 37 is in communication with inlet port 48 of sample gas passage 46. Sample gas passage 46 is connected to first gas outlet port 50 of sample gas passage 46. First gas outlet port 50 of sample gas passage 46 is connected to gas inlet port 80 of first gas mixing passage 78 through first 3-way solenoid valve 34. First gas mixing passage 78 is connected to gas outlet port 82 of first gas mixing passage 78. Gas outlet port 82 of first gas mixing passage 78 is connected to gas inlet port 74 of vacuum passage 70 through second 3-way solenoid valve 36. Gas inlet port 74 of vacuum passage 70 is connected to vacuum passage 70. Vacuum gas passage 70 is connected to gas passage 28 of vacuum source 22 at gas outlet port 72 of vacuum gas passage 70. Vacuum passage 28 is connected to vacuum source 22 at gas inlet port 24 of vacuum source 22. Carrier gas 79 is in communication with carrier gas outlet port 16 of carrier gas supply 14. Carrier gas outlet port 16 is connected to gas passage 26 of carrier gas supply 14. Gas inlet port 56 of carrier gas passage 54 is connected to gas passage 26 of carrier gas supply 14. Carrier gas passage 54 is connected to second gas outlet port 60. Second gas outlet port 60 of carrier gas passage 54 is connected to gas inlet port 86 of second gas mixing passage 84 through third 3-way solenoid valve 38. Gas inlet port 86 of second gas mixing passage 84 is connected to second gas mixing passage 84. Second gas mixing passage 84 is connected to gas outlet port 88 of second gas mixing passage 84. Gas outlet port 88 of second gas mixing passage 84 is connected to gas inlet port 68 of gas analyzer passage 62 through fourth 3-way solenoid valve 40. Gas inlet port 68 of gas analyzer passage 62 is connected to gas analyzer passage 62. Gas analyzer passage 62 is connected to gas outlet port 64 of gas analyzer passage 62. Gas outlet port 64 of gas analyzer passage 62 is connected to gas passage 30 of gas analyzer 18. Gas passage 30 of gas analyzer 18 is connected to gas inlet port 20 of gas analyzer 18 and gas inlet port 20 of gas analyzer 18 is connect to gas analyzer 18.

At the second position, shown in FIG. 2, sample gas 37 is in communication with inlet port 48 of sample gas passage 46. Sample gas passage 46 is connected to second gas outlet port 52 of sample gas passage 46. Second gas outlet port 52 of sample gas passage 46 is connected to gas inlet port 86 of second gas mixing passage 84 through third 3-way solenoid valve 38. Gas inlet port 86 of second gas mixing passage 84 is connected to second gas mixing passage 84. Second gas mixing passage 84 is connected to gas outlet port 88 of second gas mixing passage 84. Gas outlet port 88 of second gas mixing passage 84 is connected to gas inlet port 76 of vacuum gas passage 70 through fourth 3-way solenoid valve 40. Gas inlet port 76 of vacuum gas passage 70 is connected to gas outlet port 72 of vacuum gas passage 70. Gas outlet port 72 of vacuum gas passage 70 is connected to gas passage 28 of vacuum source 22. Gas passage 28 of vacuum source 22 is connected to inlet port 24 of vacuum source 22. Carrier gas 79 is in communication with carrier gas outlet port 16 of carrier gas supply 14. Carrier gas outlet port 16 is connected to gas passage 26 of carrier gas supply 14. Gas inlet port 56 of carrier gas passage 54 is connected to gas passage 26 of carrier gas supply 14. Carrier gas passage 54 is connected to first gas outlet port 58 of carrier gas passage 54. First gas outlet port 58 of carrier gas passage 54 is connected to gas inlet port 80 of first gas mixing passage 78 through first 3-way solenoid valve 34. Gas inlet port 80 of first gas mixing passage 78 is connected to first gas mixing passage 78. First gas mixing passage 78 is connected to gas outlet port 82 of first gas mixing passage 78. Gas outlet port 82 of first gas mixing passage 78 is connected to first gas inlet port 66 of gas analyzer passage 62 through second 3-way solenoid valve 36. First gas inlet port 66 of gas analyzer passage 62 is connected to gas analyzer passage 62. Gas analyzer passage 62 is connected to gas outlet port 64 of gas analyzer passage 62. Gas outlet port 64 of gas analyzer passage 62 is connected to gas passage 30 of gas analyzer 18. Gas passage 30 of gas analyzer 18 is connected to gas inlet port 20 of gas analyzer 18 and gas inlet port 20 of gas analyzer 18 is connected to gas analyzer 18.

Flush gas 103 that is being pulled into vacuum source 22 is selected from the group consisting of gas sample 37, carrier gas 79, sample gas mixture 35 and mixtures thereof and is pulled, into vacuum source 22 through gas passage 28 of vacuum source 22.

The gas carrying passages of the in-line gas monitor can be made from tubing or holes drilled in blocks of material used to fabricate the in-line gas monitor. The materials used for the in-line monitor which come in contact with the sample gas should be made from a material not corroded by or a contaminate to the sample gas.

First solenoid valve activating means 42, such as a pulsed solenoid driver, is connected to first 3-way solenoid valve 34 and second 3-way solenoid valve 36. Second solenoid valve activating means 44, such as a pulsed solenoid driver, is connected to third 3-way solenoid valve 38 and fourth second 3-way solenoid valve 40.

To continuously analyze a gas source the continuous in-line monitor sample gas inlet port is positioned at a gas sample source. Carrier gas supply is connected to the in-line monitor and a flow of carrier gas is provided. A vacuum pump is hooked up to the in-line monitor at the gas outlet port of the vacuum gas passage of the in-line monitor and turned on to provide a partial vacuum within the vacuum gas passage to draw sample gas into the in-line monitor through the sample gas passage and alternately through the first gas mixing passage and then through the second gas mixing passage of the in-line monitor. An ion trap mass spectrometer is attached to in-line monitor. The two pulsed solenoid drivers operating the four 3-way solenoid valves are activated at a duty cycle of from about 0.2 to about 0.7 seconds for activating the first position of the four 3-way solenoid valves forming the first position of the gas passages then the second position of the four 3-way solenoid valves forming the second position of the gas passages; thereby, reciprocating between the two positions. The gas sample contained in the continuous flow of sample gas coming from the in-line monitor is analyzed with the mass spectrometer.

Shown in FIG. 3 is continuous in-line gas monitoring system 400 which is another embodiment of the continuous in-line gas monitoring system of the present invention. continuous in-line gas monitoring system 400 comprises in-line monitor 402, vacuum source 404, gas analyzing means 406 and carrier gas supply means 408 for providing carrier gas 407. In-line monitor 402 comprises housing member 410 having first member 412 and second member 414, rotating member 416 contiguous within housing member 410, gas sealing means 417 for providing a gas seal between first member 412 and second member 414 of housing member 410, bearing means 418 for providing a bearing between rotating member 416 and first member 412 of housing member 410, gas seal bearing means 420, such as an "O" ring, for providing a gas seal and a bearing between housing member 410 and rotating member 416, and sample gas transfer means 422, such as an electric or pneumatic motor, for providing a rotating motion to rotating member 416 within housing member 410. Housing member 410 comprises sample gas inlet port 424, carrier gas inlet port 426, gas analyzer outlet port 428, vacuum outlet port 430, sample gas passage 432, carrier gas passage 434, gas analyzer passage 436 and vacuum passage 438. Rotating member 416 comprises first gas mixing passage 440, second gas mixing passage 442 and a sample gas transfer means 416, such as an electric or pneumatic motor driven rotating member, for transferring at a given duty cycle the sample gas from a first position to a second position of first gas mixing passage 440 and second gas mixing passage 442. Such duty cycle occurs every 180 degrees rotation of rotating member 416 in which first gas mixing passages 440 and second gas mixing passage 442 align with sample gas passage 432 and vacuum passage 438 and with carrier gas passage 434 and gas analyzer passage 436. In the first position first gas mixing passage 440 is aligned with sample gas passage 432 and vacuum passage 438 and second gas mixing passage 442 is aligned with carrier gas passage 434 and gas analyzer passage 436. In the second position first gas mixing passage 440 is aligned with carrier gas passage 434 and gas analyzer passage 436 and second mixing passage 442 is aligned with sample gas passage 432 and vacuum passage 438. The mixing of the carrier gas with the sample gas is caused by the same differential in pressures as was explained for continuous in-line gas monitoring system 10 of the present invention. The mixed carrier gas/sample gas is analyzed in gas analyzer 406, such as a ion trap mass spectrometer as described in U.S. Pat. No. 5,272,337 to Thompson et al incorporated herein by reference thereto. Sample gas mixture 403 that is being pulled into vacuum source 404 and being carried into gas analyzer 406 is selected from the group consisting of sample gas 401, carrier gas 407 and mixtures thereof. Vacuum source 404 is operatively connected to vacuum outlet port 430 of housing member 410. Gas analyzing means 406 is operatively connected to gas analyzer outlet port 428 of housing member 410. Carrier gas supply means 408 is operatively connected to carrier gas inlet port 426 of housing member 410.

While there has been shown and described what is at present considered the preferred embodiments of the invention, it will be obvious to those skilled in the art that various changes and modifications may be made therein without departing from the scope of the invention as defined by the appended claims.

We claim:

1. A continuous in-line gas monitoring system capable of accurate gas composition analysis even under strong applied vacuum conditions comprising: an in-line monitor, a source of sample gas, a carrier gas supply having a carrier gas outlet port and a supply of carrier gas, a gas analyzer having a gas inlet port and a vacuum source having a gas inlet port;

said in-line monitor comprising:
- a sample gas passage having a gas inlet port and a gas outlet port,
- a carrier gas passage having a gas inlet port and a gas outlet port,
- a gas analyzer passage having a gas outlet port and a gas inlet port,
- a vacuum passage having a gas outlet port and a gas inlet port;
- a first gas mixing passage having a gas inlet port and a gas outlet port,
- a second gas mixing passage having a gas inlet port and a gas outlet port and
- a sample gas transfer means for simultaneous positioning said first gas mixing passage and said second gas mixing passage from a first position to a second position, said first position causes positioning and connecting of said first gas mixing passage with said sample gas passage and said vacuum passage and said second gas mixing passage with said carrier gas passage and said gas analyzer passage, said second position causes positioning and connecting of said first gas mixing passage with said carrier gas passage and said gas analyzer passage and said second gas mixing passage with said sample gas passage and said vacuum passage, said positioning and connecting of said first gas mixing passage with said sample gas passage and said vacuum passage provides for said sample gas to be transferred into and through said sample gas passage, said first gas mixing passage and said vacuum passage by said vacuum source filling said first gas mixing passage with said sample gas at a reduced pressure, said positioning and connecting of said second gas mixing passage with said carrier gas passage and said gas analyzer passage provides for said carrier gas from said carrier gas source to be transferred into and through said carrier gas passage, said second gas mixing passage and said gas analyzer passage filling said second gas mixing passage with said carrier gas at a pressure greater than said reduced pressure of said sample gas contained in said first gas mixing passage, said simultaneous positioning of said first gas mixing passage and said second gas mixing passage from a first position to a second position causes said sample gas contained in said first gas mixing passage to mix with said carrier gas flowing through said carrier gas passage into said first gas mixing passage containing said sample gas and through said gas analyzer passage into said gas analyzer and causes said carrier gas contained in said second gas mixing passage to mix with said sample gas flowing through said sample gas passage into said second gas mixing passage containing said carrier gas and through said vacuum passage into said vacuum source, a reciprocating of said simultaneous positioning of said first gas mixing passage and said second gas mixing passage through a sufficient duty cycle rate that causes a mixing of said sample gas with said carrier gas forming a sample gas mixture because of a difference in said gas pressure of said sample gas and said gas pressure of said carrier gas, at said first position said sample gas is in communication with said inlet port of said sample gas passage, said gas outlet port of said sample gas passage is connected to said gas inlet port of said first gas mixing passage, said gas outlet port of said first gas mixing passage is connected to said gas inlet port of said vacuum passage and said gas outlet port of said vacuum passage is connected to said gas inlet port of said vacuum source and said gas inlet port of said carrier gas passage is connected to said gas outlet port of said supply of carrier gas, said gas inlet port of said second gas mixing passage is connected to said gas outlet port of said carrier gas passage, said outlet port of said second gas mixing passage is connected to said gas inlet port of said gas analyzer passage, said gas outlet port of said gas analyzer passage is connected to said gas inlet port of said gas analyzer, at said second position said sample gas is in communication with said inlet port of said sample gas passage, said gas outlet port of said sample gas passage is connected to said gas inlet port of said second gas mixing passage, said gas outlet port of said second gas mixing passage is connected to said gas inlet port of said vacuum passage and said gas outlet port of said vacuum passage is connected to said gas inlet port of said vacuum source and said gas inlet port of said carrier gas passage is connected to said gas outlet port of said supply of carrier gas, said gas inlet port of said first gas mixing passage is connected to said gas outlet port of said carrier gas passage, said outlet port of said first gas mixing passage is connected to said gas inlet port of said gas analyzer passage, said gas outlet port of said gas analyzer passage is connected to said gas inlet port of said gas analyzer.

2. A continuous in-line gas monitoring system in accordance with claim 1 wherein said sample gas transfer means are 3-way solenoid valves in communication with valve activating means.

3. A continuous in-line gas monitoring system in accordance with claim 1 wherein said carrier gas is helium.

4. A continuous in-line gas monitoring system in accordance with claim 1 wherein said gas analyzer is a mass spectrometer having an ion trap.

5. A continuous in-line gas monitoring system in accordance with claim 1 wherein said vacuum source is a vacuum pump.

6. A continuous in-line gas monitoring system in accordance with claim 2 wherein valve activating means are pulsed solenoid drivers.

7. A continuous in-line gas monitoring system in accordance with claim 1 wherein said sample gas passage, said carrier gas passage, said gas analyzer passage, said vacuum passage, said first gas mixing passage and said second gas mixing passage are gas carrying passages.

8. A method for continuously analyzing a gas sample with a gas analyzer comprising the following steps:

Step 1—providing a continuous in-line gas monitoring system capable of accurate gas composition analysis even under strong applied vacuum conditions; said continuous in-line gas monitoring system comprising: an in-line monitor, a source of sample gas, a supply of carrier gas having a carrier gas outlet port, a gas analyzer having a gas inlet port and a vacuum source having a gas inlet port;

said in-line monitor comprising:
a sample gas passage having a gas inlet port and a gas outlet port,
a carrier gas passage having a gas inlet port and a gas outlet port,
a gas analyzer passage having a gas outlet port and a gas inlet port,
a vacuum passage having a gas outlet port and a gas inlet port;
a first gas mixing passage having a gas inlet port and a gas outlet port,
a second gas mixing passage having a gas inlet port and a gas outlet port and
a sample gas transfer means for simultaneous positioning said first gas mixing passage and said second gas mixing passage from a first position to a second position, said first position causes positioning and connecting of said first gas mixing passage with said sample gas passage and said vacuum passage and said second gas mixing passage with said carrier gas passage and said gas analyzer passage, said second position causes positioning and connecting of said first gas mixing passage with said carrier gas passage and said gas analyzer passage and said second gas mixing passage with said sample gas passage and said vacuum passage, said positioning and connecting of said first gas mixing passage with said sample gas passage and said vacuum passage provides for said sample gas to be transferred into and through said sample gas passage, said first gas mixing passage and said vacuum passage by said vacuum source filling said first gas mixing passage with said sample gas at a reduced pressure, said positioning and connecting of said first gas mixing passage with said carrier gas passage and said gas analyzer passage provides for said carrier gas from said carrier gas source to be transferred into and through said carrier gas passage, said second gas mixing passage and said gas analyzer passage filling said second gas mixing passage with said carrier gas at a pressure greater than said reduced pressure of said sample gas contained in said first gas mixing passage, said simultaneous positioning of said first gas mixing passage and said second gas mixing passage from a first position to a second position causes said sample gas contained in said first gas mixing passage to mix with said carrier gas flowing through said carrier gas passage into said first gas mixing passage containing said sample gas and through said gas analyzer passage into said gas analyzer and causes said carrier gas contained in said second gas mixing passage to mix with said sample gas flowing through said sample gas passage into said second gas mixing passage containing said carrier gas and through said vacuum passage into said vacuum source, a reciprocating of said simultaneous positioning of said first gas mixing passage and said second gas mixing passage through a sufficient duty cycle rate that causes a mixing of said sample gas with said carrier gas forming a sample gas mixture because of a difference in said gas pressure of said sample gas and said gas pressure of said carrier gas, at said first position said sample gas is in communication with said inlet port of said sample gas passage, said gas outlet port of said sample gas passage is connected to said gas inlet port of said first gas mixing passage, said gas outlet port of said first gas mixing passage is connected to said gas inlet port of said vacuum passage and said gas outlet port of said vacuum passage is connected to said gas inlet port of said vacuum source and said gas inlet port of said carrier gas passage is connected to said gas outlet port of said supply of carrier gas, said gas inlet port of said second gas mixing passage is connected to said gas outlet port of said carrier gas passage, said outlet port of said second gas mixing passage is connected to said gas inlet port of said gas analyzer passage, said gas outlet port of said gas analyzer passage is connected to said gas inlet port of said gas analyzer, at said second position said sample gas is in communication with said inlet port of said sample gas passage, said gas outlet port of said sample gas passage is connected to said gas inlet port of said second gas mixing passage, said gas outlet port of said second gas mixing passage is connected to said gas inlet port of said vacuum passage and said gas outlet port of said vacuum passage is connected to said gas inlet port of said vacuum source and said gas inlet port of said carrier gas passage is connected to said gas outlet port of said supply of carrier gas, said gas inlet port of said first gas mixing passage is connected to said gas outlet port of said carrier gas passage, said outlet port of said first gas mixing passage is connected to said gas inlet port of said gas analyzer passage, said gas outlet port of said gas analyzer passage is connected to said gas inlet port of said gas analyzer;

Step 2—positioning said inlet port of said sample gas passage at a source of sample gas;

Step 3—providing a flow of said carrier gas into said carrier gas passage;

Step 4—providing said vacuum source at said gas outlet port of said vacuum passage;

Step 5—providing said gas analyzer at said gas outlet port of said gas analyzer passage;

Step 6—activating said sample gas transfer means to simultaneously position said first gas mixing passage and said second gas mixing passage from said first position to said second position in a reciprocating fashion to provide a continuous flow of said sample gas, a continuous mixing of said carrier gas with said sample gas forming a sample gas mixture and a continuous flow of said sample gas mixture to said gas analyzer; and Step 7—analyzing said sample gas contained in said sample gas mixture with said gas analyzer.

9. A method in accordance with claim 8 wherein said sample gas transfer means are solenoid valves in communication with pulsed solenoid drivers.

10. A method in accordance with claim 8 wherein said carrier gas is helium.

11. A method in accordance with claim 8 wherein said gas analyzer is a mass spectrometer having an ion trap.

12. A method in accordance with claim 8 wherein said vacuum source is a vacuum pump.

13. A method in accordance with claim 9 wherein said valve activating means are pulsed solenoid drivers.

14. A method in accordance with claim 8 wherein said sample gas passage, said carrier gas passage, said gas analyzer passage, said vacuum passage, said first gas mixing passage and said second gas mixing passage are gas carrying passages.

15. A method in accordance with claim 8 wherein said activating of said sample gas transfer means in Step 6 is in a duty cycle of about 0.2 to about 0.7 seconds.

16. A continuous in-line gas monitoring system in accordance with claim 1 wherein said in-line monitor comprises:

a housing member having a first member and a second member, a rotating member contiguous within said housing member, a gas sealing means for providing a gas seal between said first member and said second member of said housing member, a bearing means for providing a bearing between said rotating member and said first member of said housing member, a gas seal bearing means for providing a gas seal and a bearing between said housing member and said rotating member, and a sample gas transfer means for providing a rotating motion to said rotating member within said housing member;

said housing member comprises: a sample gas inlet port, a carrier gas inlet port, a gas analyzer outlet port, a vacuum outlet port, a sample gas passage, a carrier gas passage, a gas analyzer passage and a vacuum passage;

said rotating means comprises: a first gas mixing passage, a second gas mixing passage and a sample gas transfer means for transferring at a given duty cycle said sample gas from a first position to a second position of said first gas mixing passage and said second gas mixing passage;

said vacuum source being operatively connected to said vacuum outlet port of said housing member;

said gas analyzing means being operatively connected to said gas analyzer outlet port of said housing member; and said carrier gas supply means being operatively connected to said carrier gas inlet port of said housing member.

17. A continuous in-line gas monitoring system in accordance with claim 16 wherein said gas seal bearing means is an "O" ring.

18. A continuous in-line gas monitoring system in accordance with claim 16 wherein said sample gas transfer means is an electric motor.

19. A continuous in-line gas monitoring system in accordance with claim 16 wherein said sample gas transfer means is a pneumatic motor.

20. A method for continuously analyzing a gas sample with a gas analyzer in accordance with claim 8 wherein said Step 1 is providing a continuous in-line gas monitoring system;

said continuous in-line gas monitoring system comprising: an in-line monitor, a source of sample gas, a supply of carrier gas having a carrier gas outlet port, a gas analyzer having a gas inlet port and a vacuum source having a gas inlet port;

said in-line monitor comprising:
a housing member having a first member and a second member,
a rotating member contiguous within said housing member,
a gas sealing means for providing a gas seal between said first member and said second member of said housing member,
a bearing means for providing a bearing between said rotating member and said first member of said housing member,
a gas seal bearing means for providing a gas seal and a bearing between said housing member and said rotating member, and a sample gas transfer means for providing a rotating motion to said rotating member within said housing member;

said housing member comprising: a sample gas inlet port, a carrier gas inlet port, a gas analyzer outlet port, a vacuum outlet port, a sample gas passage, a carrier gas passage, a gas analyzer passage and a vacuum passage;

said rotating means comprising: a first gas mixing passage, a second gas mixing passage and a sample gas transfer means for transferring at a given duty cycle said sample gas from a first position to a second position of said first gas mixing passage and said second gas mixing passage;

said vacuum source being operatively connected to said vacuum outlet port of said housing member;

said gas analyzing means being operatively connected to said gas analyzer outlet port of said housing member; and said carrier gas supply means being operatively connected to said carrier gas inlet port of said housing member; and said Step 6 is activating said sample gas transfer means to simultaneously position said first gas mixing passage and said second gas mixing passage from said first position to said second position to provide a continuous flow of said sample gas, a continuous mixing of said carrier gas with said sample gas forming a sample gas mixture and a continuous flow of said sample gas mixture to said gas analyzer.

\* \* \* \* \*